(12) United States Patent (10) Patent No.: US 8,095,388 B2
Masuzawa et al. (45) Date of Patent: Jan. 10, 2012

(54) MEDICAL IMAGING DIAGNOSIS SUPPORTING APPARATUS AND IMAGE DIAGNOSIS SUPPORTING METHOD

(75) Inventors: Takashi Masuzawa, Otawara (JP); Kenji Matsue, Nasushiobara (JP); Kenichi Niwa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 825 days.

(21) Appl. No.: 11/682,595

(22) Filed: Mar. 6, 2007

(65) Prior Publication Data
US 2007/0239489 A1 Oct. 11, 2007

(30) Foreign Application Priority Data
Mar. 7, 2006 (JP) .................. 2006-061499

(51) Int. Cl.
*G06F 19/00* (2011.01)
*G06Q 50/00* (2006.01)
(52) U.S. Cl. ......................................... 705/3
(58) Field of Classification Search .................. 705/2, 3; 709/206; 364/514 R
See application file for complete search history.

(56) References Cited

U.S. PATENT DOCUMENTS

| 5,557,541 A * | 9/1996 | Schulhof et al. ............... 700/94 |
| 6,424,996 B1 * | 7/2002 | Killcommons et al. ...... 709/206 |
| 2004/0071038 A1 * | 4/2004 | Sterritt ........................... 365/232 |

FOREIGN PATENT DOCUMENTS

| CN | 1500442 A | 6/2004 |
| JP | 9-6867 | 1/1997 |
| JP | 9-81646 | 3/1997 |
| JP | 11-143956 | 5/1999 |
| JP | 2002-297767 | 10/2002 |
| JP | 2003-93348 | 4/2003 |
| JP | 2004-154560 | 6/2004 |

OTHER PUBLICATIONS

U.S. Appl. No. 12/260,395, filed Oct. 29, 2008, Futami, et al.
U.S. Appl. No. 12/100,736, filed Apr. 10, 2008, Matsue, et al.
U.S. Appl. No. 12/107,356, filed Apr. 22, 2008, Kazuno, et al.
U.S. Appl. No. 12/100,780, filed Apr. 10, 2008, Kazuno, et al.
Office Action issued Feb. 8, 2011, in Japanese Patent Application No. 2006-061499 with English translation.

* cited by examiner

*Primary Examiner* — Gerald J. O'Connor
*Assistant Examiner* — John Pauls
(74) *Attorney, Agent, or Firm* — Oblon, Spivak, McClelland, Maier & Neustadt, L.L.P.

(57) ABSTRACT

By selecting at least one of an image and a report to be provided for an institute to which a patient is introduced, an object having the same series ID as that of the image or report is automatically obtained. Medical information including the object is generated and stored in an external medium. By selecting an image or the like to be provided to the institute to which a patient is introduced, address information of the selected image or the like and address information of an object or the like having the same series ID as that of the image or the like is automatically obtained. Medical information including the address information is generated and stored in an external medium.

26 Claims, 10 Drawing Sheets

Communication environment information table

| Institute to which patient is introduced | Line speed | Security level |
|---|---|---|
| A | M | M |
| B | L | M |
| C | H | H |
| ⋮ | | |

H: High(high speed or high-level safety)
M: Middle(intermediate speed or intermediate-level safety)
L: Low(low speed or low-level safety)

F I G. 8

| Table for report | | | | |
|---|---|---|---|---|
| | | Line speed | | |
| | | L | M | H |
| Security level | L | — | — | — |
| | M | ○ | ○ | ○ |
| | H | ○ | ○ | ○ |

○: Shows that report can be provided via network
—: Shows that report cannot be provided via network

FIG. 9

| Table for image | | | | |
|---|---|---|---|---|
| | | Line speed | | |
| | | L | M | H |
| Security level | L | — | — | — |
| | M | ○ | — | — |
| | H | ○ | ○ | ○ |

○: Shows that image can be provided via network
—: Shows that image cannot be provided via network

FIG. 10

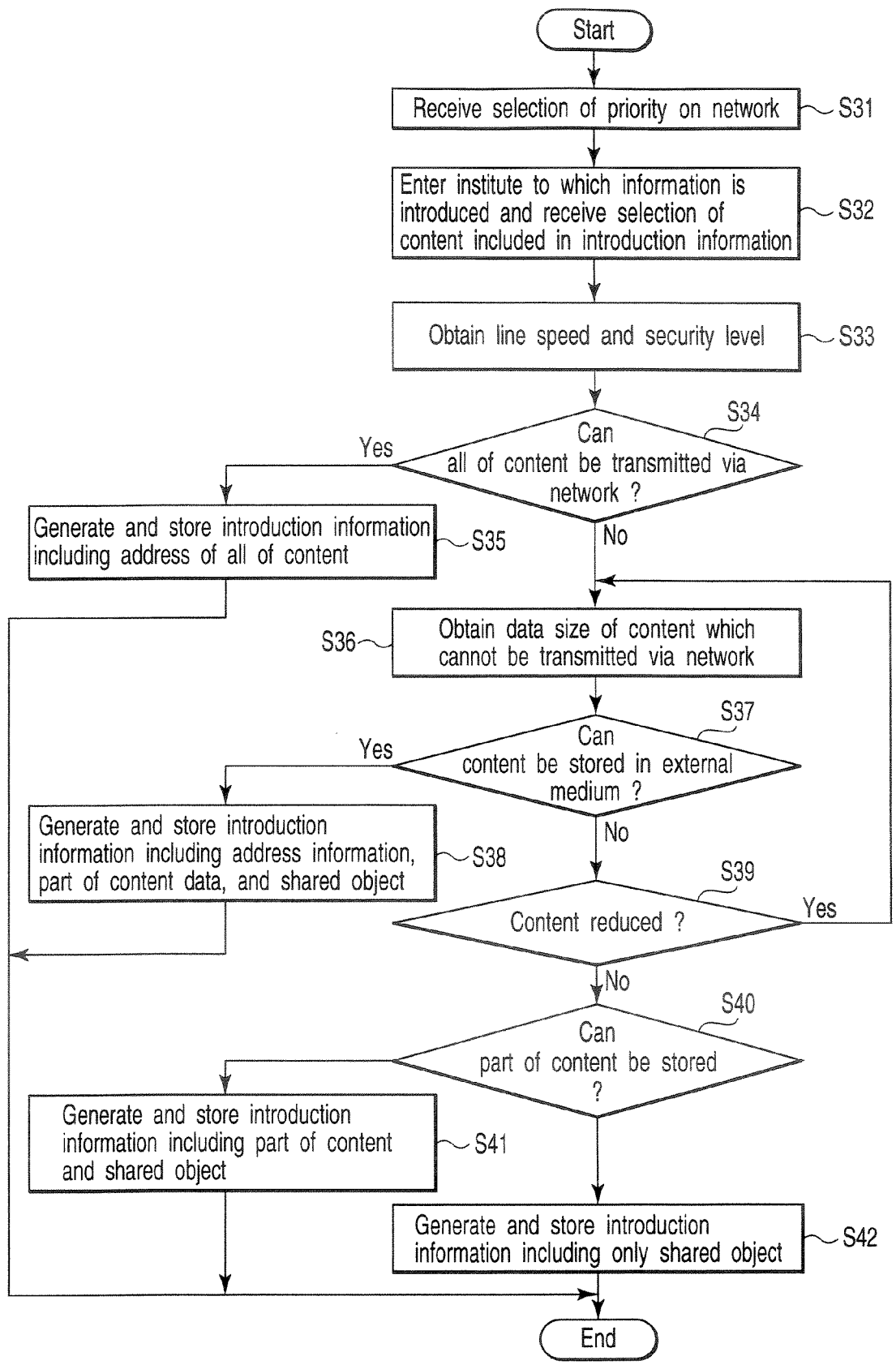
F I G. 12

US 8,095,388 B2

MEDICAL IMAGING DIAGNOSIS SUPPORTING APPARATUS AND IMAGE DIAGNOSIS SUPPORTING METHOD

CROSS-REFERENCE TO RELATED APPLICATIONS

This application is based upon and claims the benefit of priority from prior Japanese Patent Application No. 2006-061499, filed Mar. 7, 2006, the entire contents of which are incorporated herein by reference.

BACKGROUND OF THE INVENTION

1. Field of the Invention

The present invention relates to an imaging diagnosis supporting system and, more particularly, to a medical imaging diagnosis supporting apparatus and an imaging diagnosis supporting method used when data is transmitted/received among a plurality of apparatuses.

2. Description of the Related Art

In recent years, a medical activity is finely divided. For example, image diagnosis is divided into works of generation of an examination order of a patient, acquisition of diagnostic images based on the generated order, reading of the acquired diagnostic images and generation of a report, and explanation of the diagnosis result and treatment course on the basis of the report. Each of the works is done by an expert (medical doctor or medical technologist), and a medical activity such as diagnosis for a patient is achieved by all of the works. Each of the experts executes his/her work on the basis of information generated by the other experts in the preceding works and by properly referring to diagnostic information and the like in the past.

In the process of such medical imaging diagnosis, there is a case that the medical institute of the patient is changed to another medical institute. In this case, the introducing-side medical institute records predetermined information on a portable medium, and the another medical institute succeeds the diagnosis on the basis of the information recorded on the medium.

The conventional method, however, has the following problems. Even if a patient is introduced with images, there is a case that the another institute cannot use the images due to incompatibility of an examination apparatus or the model. When there are many images, all of even key images cannot be stored in some media, so that they cannot be given to the another institute. Further, when medical images and the like as personal information are recorded on a medium, a problem on security such as information leakage may occur.

BRIEF SUMMARY OF THE INVENTION

The present invention has been achieved in consideration of the above-described circumstances and an object of the invention is to provide a medical imaging diagnosis supporting apparatus and an imaging diagnosis supporting method of generating preferable introduction information of a patient from an introducing-side medical institution to another medical institution from the medical viewpoints and the like, and capable of determining whether various information is provided from the introducing-side medical institution to another medical institution or not, an information providing method, and content of introduction information from the viewpoint of capability of network environment and security against information leakage.

According to an aspect of the present invention, it is provided that a medical imaging diagnosis supporting apparatus comprising: a selecting unit which selects at least one of an image and a report of a patient; an extracting unit which extracts an object including a positioning image or imaging parameter information associated with at least one of the selected image and report from a storing device which stores a plurality of objects each including a positioning image and imaging parameter information; and a generating unit which generates medical information based on the extracted object.

According to another aspect of the present invention, it is provided that a medical imaging diagnosis supporting method comprising: selecting at least one of an image and a report of a patient; extracting an object including a positioning image or imaging parameter information associated with at least one of the selected image and report from a storing device which stores a plurality of objects each including a positioning image and imaging parameter information; and generating medical information based on the extracted object.

BRIEF DESCRIPTION OF THE SEVERAL VIEWS OF THE DRAWING

FIG. 8 is a communication environment information table showing that line speed and security level of each of hospitals to which patients are to be introduced, in three levels of L (low level), M (intermediate level), and H (high level);

FIG. 9 is a table for a report, indicating whether a report can be transmitted via a network or not on the basis of the relation between line speed and security level;

FIG. 10 is a table for an image, indicating whether an image can be transmitted via a network or not on the basis of the relation between line speed and security level;

FIG. 12 is a flowchart showing the flow of introduction information determining process in the case where priority is placed on a network.

DETAILED DESCRIPTION OF THE INVENTION

Figure 1:
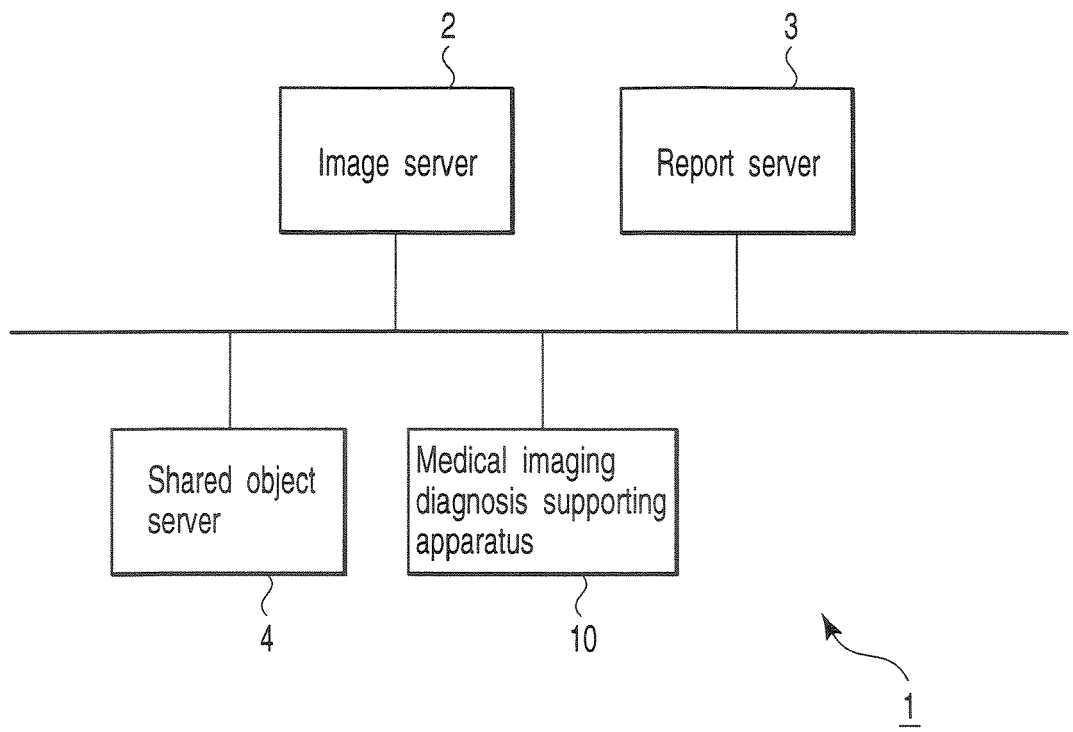
FIG. 1 is a block diagram showing the configuration of a medical diagnostic imaging supporting system 1 according to a first embodiment.

First to third embodiments of the present invention will be described below with reference to the drawings. In the following description, the same reference numerals are designated to components having the same or similar functions and configurations, and repetitive description will be given only when needed.

First Embodiment

FIG. 1 is a block diagram showing the configuration of a medical diagnostic imaging support system 1 according to the present embodiment. As shown in the diagram, the medical diagnostic imaging support system 1 has an image server 2, a report server 3, a shared object server 4, and a medical imaging diagnosis supporting apparatus 10.

The image server 2 manages images generated by various medical diagnostic imaging apparatuses, images generated by post-process by an image viewing apparatus 7, and the like by using series IDs, patient IDs, dedicated management IDs, and the like. A series is a concept for managing various information by time (when information is generated), space (where information is generated), and an clinical characteristic of information (clinical meaning). Therefore, for example, a plurality of CT images captured by a single scan in an examination using an X-ray CT apparatus are information belonging to the same series. A series ID is an identification number assigned to various information belonging to the same series.

The image server 2 stores an image address table showing the correspondence relations between address information (for example, IP addresses) indicative of the locations of images on a network and dedicated management IDs and the like. When a request for the address information of a predetermined image is received from the medical imaging diagnosis supporting apparatus 10, the image server 2 obtains the address information of a corresponding image on the basis of the dedicated management ID of the image and the image address table and, as necessary, transmits the address information to the medical imaging diagnosis supporting apparatus 10.

The report server 3 manages reports generated by the image viewing apparatus, a report generation terminal, and the like by series IDs, patient IDs, dedicated management IDs, or the like.

The report server 3 stores a report address table indicative of the correspondence relations between address information of locations of reports on a network and dedicated management IDs and the like. When a request for the address information of a predetermined report is received from the medical imaging diagnosis supporting apparatus 10, the report server 3 obtains the address information of a corresponding report on the basis of the dedicated management ID of the report and the report address table and, as necessary, transmits the address information to the medical imaging diagnosis supporting apparatus 10.

The shared object server 4 manages and stores shared objects by the patient IDs, series IDs, dedicated management IDs, or the like. The shared objects are information for effectively utilizing information (for example, positioning images, imaging positions, imaging ranges, imaging parameters, image generating parameters, and the like) used for past medical treatments. The shared object will be described in detail later.

The shared object server 4 also stores a shared object address table indicative of correspondence relations between address information of locations of shared objects on a network and dedicated management IDs and the like. When a request for the address information of a predetermined shared object is received from the medical imaging diagnosis supporting apparatus 10, the shared object server 4 obtains the address information of a corresponding shared object on the basis of the dedicated management ID of the shared object and the shared object address table and, as necessary, transmits the address information to the medical imaging diagnosis supporting apparatus 10.

Figure 2:
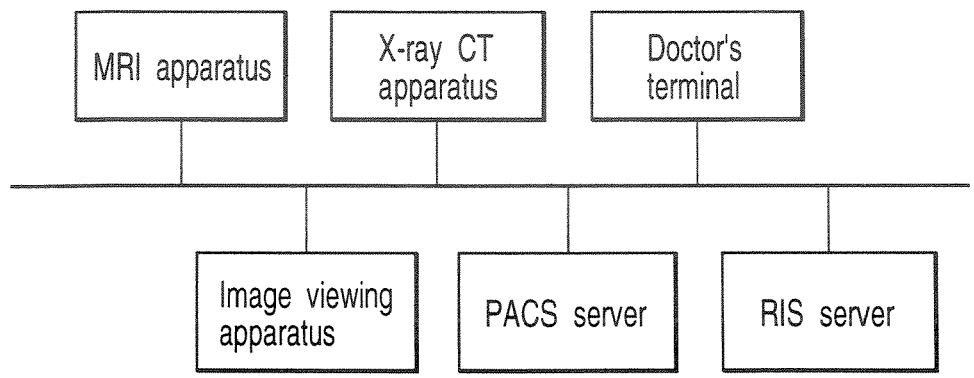
FIG. 2 is a diagram showing a doctor's terminal, an image viewer, a medical diagnostic imaging apparatus (X-ray CT (Computed-Tomography) apparatus or MRI (Magnetic Resonance Imaging) apparatus), and the like connected to a network in a hospital.

In the case of introducing a patient to another medical institute, the medical imaging diagnosis supporting apparatus 10 generates medical information effectively used for diagnosing the patient in the another medical institute as introduction information, and records the medical information to an external medium (magnetic disk (floppy disk, hard disk, or the like), optical disk (CD-ROM, DVD, or the like), or a portable medium such as a semiconductor memory). As the medical imaging diagnosis supporting apparatus 10, a dedicated single apparatus may be provided. Alternatively, for example, as shown in FIG. 2, the medical imaging diagnosis supporting apparatus 10 may be built in any of a doctor's terminal, an image viewing apparatus (viewer), a report generation support system, medical diagnostic imaging apparatuses (X-ray CT apparatus and MRI apparatus), a PACS (Picture Archiving and Communication System) server, and an RIS (Radiology Information System) server connected to a hospital network, a PACS, an RIS, or the like.

Figure 3:
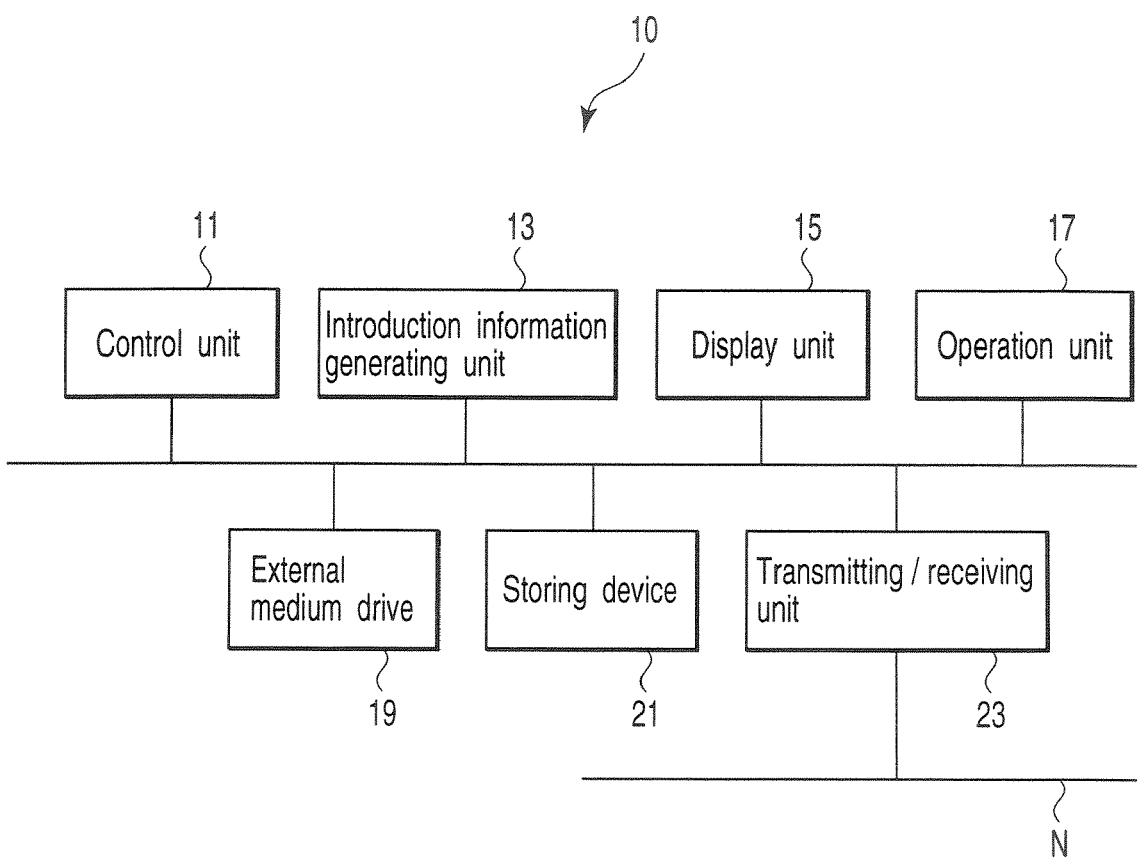
FIG. 3 is a block diagram showing the configuration of a medical imaging diagnosis supporting apparatus 10.

FIG. 3 is a block diagram showing the configuration of the medical imaging diagnosis supporting apparatus 10. As shown in the diagram, the medical imaging diagnosis supporting apparatus 10 has a control unit 11, an introduction information generating unit 13, a display unit 15, an operation unit 17, an external medium drive 19, a storing device 21, and a transmitting/receiving unit 23.

The control unit 11 controls static or dynamic operation of the medical imaging diagnosis supporting apparatus 10 in a centralized manner. The control unit 11 develops a dedicated program stored in the storing device 21 on a not-shown memory, thereby realizing an introduction information generating function and the like.

The introduction information generating unit 13 realizes a process according to the introduction information generating function (introduction information generating process) which will be described later under the control of the control unit 11.

The display unit 15 displays, in a predetermined form, an interactive screen or the like for instructing the structure of introduction information, instructing a medium or network on which priority is placed, and the like in the introduction information generating process.

The operation unit 17 is a device having a keyboard, various switches, a mouse, and the like, to which an instruction from the operator can be input. Content to be included in the introduction information is selected by using the operation unit 17.

The external medium drive 19 records predetermined information such as introduction information to an inserted external medium.

The storing device 21 stores a dedicated program for realizing the introduction information generating function and the like.

The transmitting/receiving unit 23 transmits/receives image data, patient information, and the like to/from other devices via a network N. In particular, the transmitting/receiving unit 23 receives image data, a report, and a shared object from the image server 2, the report server 3, and the shared object server 4, respectively, via the network N.

(Introduction Information Generating Function)

Next, the introduction information generating function of the medical imaging diagnosis supporting apparatus 10 will be described. The introduction information is information useful in diagnosis of the patient introduced to another medical institute and includes at least a shared object and, as necessary, an image and a report of the patient. Which information (content) is included in the introduction information is determined by the operator or the medical imaging diagnosis supporting apparatus 10 in the medical institute introducing the patient. Various information as components of the introduction information will be described below.

[Image]

An image included in the introduction information is an image determined to be desirably provided to another medical institute by the introducing medical institute or an image requested by another medical institute. Typical examples are a key image (key images) based on which a disease was diagnosed, a key image and a plurality of images preceding and subsequent to the key image in a predetermined range, all of images in the same series including the key image, all of images captured in an examination (examination images), and all of images (patient images) captured in a current examination or past examinations of the patient.

[Report]

A report included in the introduction information is a report determined by an introducing medical institute that it is preferred to be provided to a medical institute to which a patient is introduced, or a report that an introducing medical institute is requested to submit by a medical institute to which a patient is introduced. As necessary, a key image or the like is linked or attached to the report. The embodiment is not limited to the presence or absence of a link or attachment of a key image.

[Shared Object]

The shared object is constructed by image information and supplementary information (characters or numerical values) to effectively use information (for example, positioning images, imaging positions, imaging ranges, imaging parameters, image generating parameters, and the like) used for past medical treatments. The shared object is generated as an entity of information (for example, a file) separated from normal image data, and is stored and managed.

Figure 4:
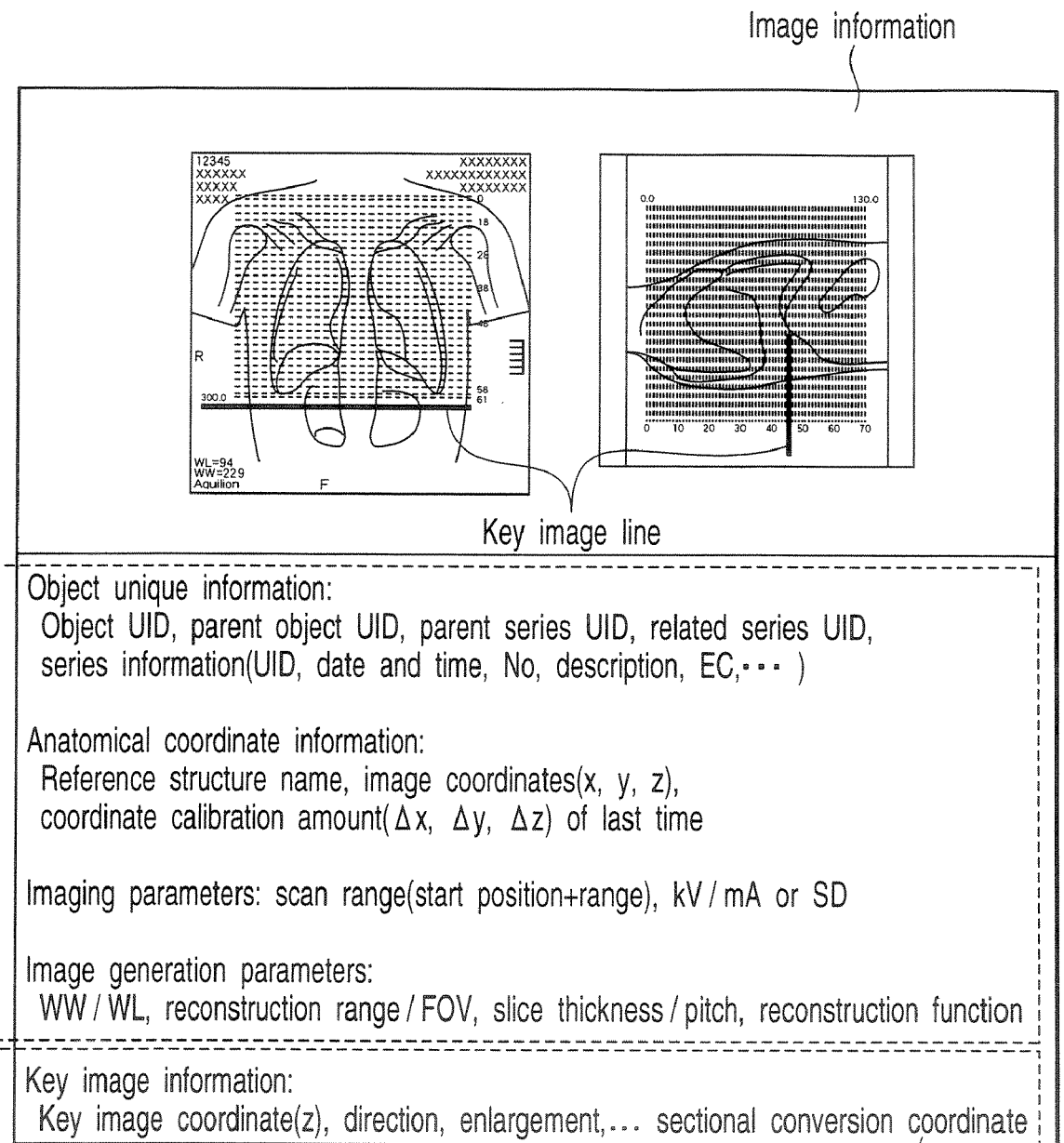
FIG. 4 is a diagram showing an example of the configuration of a shared object.

FIG. 4 is a diagram showing an example of the configuration of a shared object. As shown in the diagram, the shared object has image information and supplementary information. Each of the image information and the supplementary information constructing the shared object will be described below.

[Image Information]

Image information of the shared object is one or plural positioning images indicative of an imaging range (for example, scannogram used by an X-ray CT apparatus, a scout view used in an MRI apparatus, or the like). The imaging range denotes here a physical range to be detected for signals by a detector on the basis of energy actually supplied by the medical diagnostic imaging apparatus by X-ray, high frequency, or the like. For example, in the case of an X-ray CT apparatus, the imaging range is a range (scan range) in the body axis direction, exposed with an X-ray generated by an X-ray tube and in which the X-ray is detected by a detector. Generally, the imaging range is clearly shown by dotted lines or the like on a positioning image acquired by imaging the whole body.

[Supplementary Information]

The supplementary information of the shared object can be largely classified into five kinds of information; object unique information, anatomical coordinate information, imaging parameters, image generation parameters, and key image information. Each of the five kinds of information will be described below.

[Supplementary Information 1: Unique Information of Object]

The object's unique information is information indicative of relationship of the object with other objects in order to distinguish the object from the other objects. The object unique information includes an object ID (object UID), a parent object ID (parent object UID), a related-series ID (related-series UID), and the series ID (the series UID).

The object UID is information for distinguishing the object from the other objects. The object UIDs are generated by a system which is not used at the time of generating a shared object by an object generating unit in each apparatus. The parent object UID is information for specifying an object (parent object) referred to at the time of generating the object. The related-series UID is information for specifying a series using the same parameters (for example, the imaging parameters, positioning image, and the like) as those of the shared object. In some cases, a plurality of related-series UIDs exist in the object unique information by its nature. In those cases, preferably, supplementary information of the series (date and time of the series, series number, series description, and kind of contrast medium) and the like is also associated with the series UID. With such a configuration, only by referring to the shared object, information identified by the operator can be obtained without retrieving a group of actual images. The series UID is an identifier for specifying the series whose imaging parameters and the like are indicated by the shared object.

Data specified by a UID is linked. Therefore, by accessing the linked data on the basis of the UID, derivative examination progresses of the image group can be promptly tracked.

[Supplementary Information 2: Anatomical Coordinate Information]

The anatomical coordinate information is information of coordinates using the human body structure on an image as a reference (human body reference coordinates) different from a coordinate system of a group of images acquired by a scan (generally, coordinates of devices using the absolute bed position or relative bed position as a reference). The human body reference coordinates are automatically generated by the apparatus for generating a shared object.

Figure 5A:
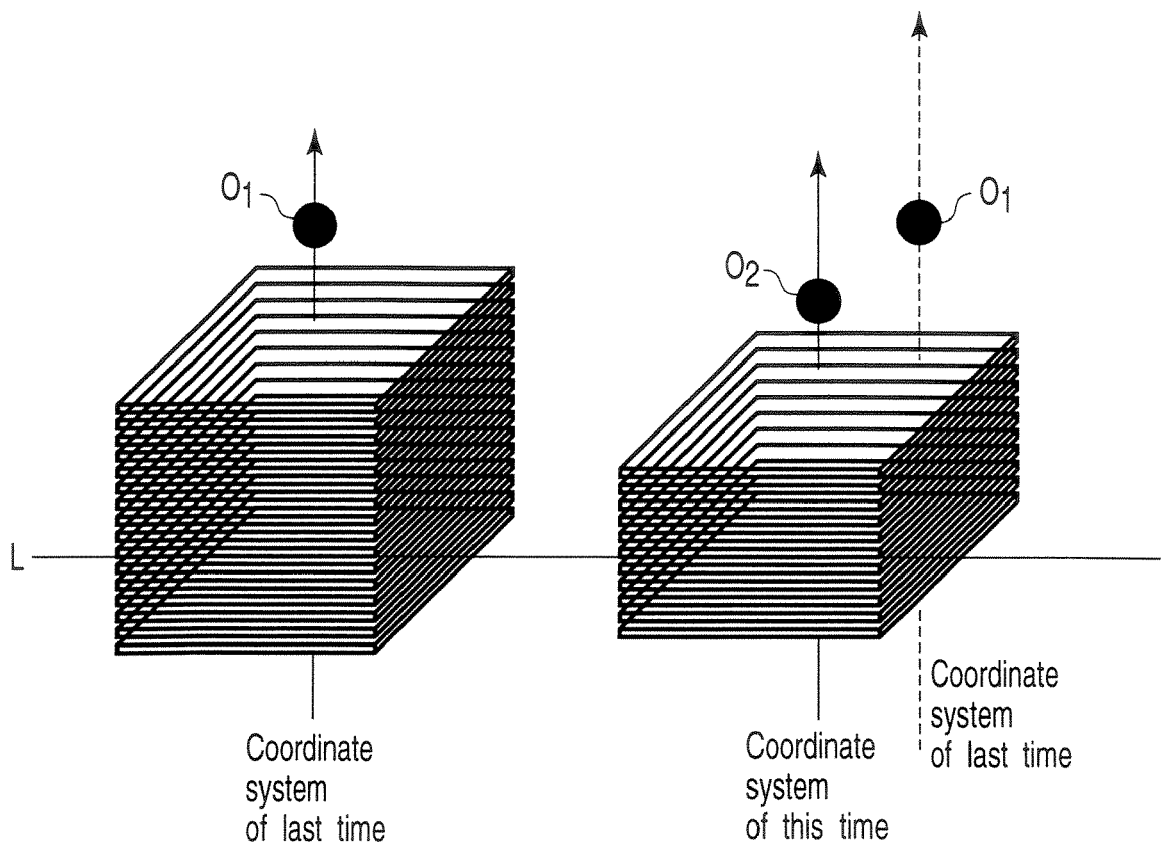
FIGS. 5A and 5B are diagrams showing the concept of human body reference coordinates of a shared object.
Figure 5B:
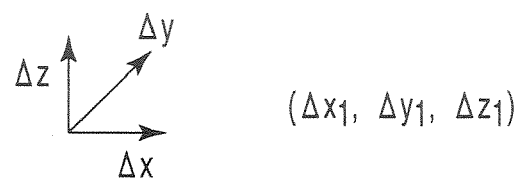

FIGS. 5A and 5B are diagrams for explaining the concept of the human body reference coordinates. In FIG. 5A, it is assumed that a slice image was acquired in a position apart from a reference point (for example, OM line, pelvis, or the pit of the stomach (epigastric region)) O1 in the anatomical coordinate system of last time by distance L. In this case, as shown in FIG. 5B, the same position as that in the slice image of last time can be specified on the basis of a coordinate calibration amount ($\Delta x$, $\Delta y$, $\Delta z$) as a deviation amount between the reference point O1 and a reference point O2 of the coordinate system of this time (in the same position as that of the reference point O1 from the anatomical viewpoint) and the distance L from the reference point. Therefore, from the anatomical coordinate information, a position which has to be reproduced in the next examination or film reading, such as the imaging range, the coordinates of key image information, or the like can be specified from the anatomic viewpoint.

The position information in the anatomical coordinate information is not limited to the above examples. For example, in the case of performing calibration including enlargement and rotation other than calibration using the calibration amount ($\Delta x$, $\Delta y$, $\Delta z$) of the coordinate system, an enlargement ratio a or rotation angle ($\beta$, $\theta$) is not limited to one reference point. A positional deviation ($\Delta x2$, $\Delta y2$, $\Delta z2$) from another reference point may be also included in the anatomical coordinate information.

A combination of the anatomical structural name and a positioning image coordinate system (the upper left point of image data is (0, 0)) as the reference point of coordinates may be also held as information different from the calibration amount. The anatomical reference point can be added by a function of obtaining and storing position information designated by an operator when image display means such as an image viewer of a modality or PACS is provided. By using the function, an anatomical reference point can be drawn on a positioning image of a examination of last time. The operator designates the same anatomical structure in a positioning image of a examination of this time while seeing the reference point, and an examiner can easily recognize a deviation from the coordinate system of last time, that is, a coordinate system calibration amount.

It is preferable to select an anatomical reference point in a portion where a positional change due to a physiologic movement such as respiration or beating is small. Concrete examples of the anatomical reference point are centrum of the lower border of a twelfth thoracic vertebra, iliac spine, iliac crest, inferior margin of the symphysis pubis, and inferior margin of the bifurcation tracheae. Since a structure is determined by a human, the names are stored. In the case of using a technique of automatically identifying an internal organ from an image, identifiers of structures which can be recognized by a computer may be used. Such a technique is studied and disclosed in "Intelligent Assistance in Diagnosis of Multi-dimensional Medical Images", Grant-in-Aid for Scientific Research on Priority Areas, (http://www.future-cad.org/fcad/index_j.htm).

[Supplementary Information 3: Imaging Parameters]

Imaging parameters are physical parameters necessary to collect physical data from which an image is generated from a patient by imaging operation. The parameters depend on the kind of a modality. For example, imaging parameters of an X-ray CT apparatus are physical amounts such as a scan start position and range (bed movement amount), KV/mA of an X-ray tube, and a bed movement amount (beam pitch) per rotation with respect to the total width of an image slice acquired. However, the imaging parameters are not limited to the above examples. For example, a subject insertion direction at the time of an examination (information that a subject is inserted in the apparatus from the feet or the head), whether a contrast medium is administered or not, dose of the contrast medium, the kind of the medium, the body posture of the patient (whether the patient lies with his/her face down or up) may be included. Further, recently, there is the function of automatically controlling KV/mA so that predetermined picture quality is obtained in order to reduce exposure. In such a case, image noise (SD value) as a control amount may be included in the imaging parameters.

For example, in the case of an MRI apparatus, the imaging parameters may include parameters such as the imaging range, the insertion direction and the posture of a patient, intensity of magnetic field, pulse sequence, the kind of a detection coil, the installation position of the detection coil, the presence/absence of gate cardio imaging or respiratory gated imaging, the presence/absence of air supply to the bed, a body region in the center of imaging, and an attachment position.

[Supplementary Information 4: Image Generation Parameters]

The image generation parameters are parameters for reconstructing an image from physical data obtained by imaging, i.e., filter process parameters such as a reconstruction range, time phase, the position, direction, and thickness of an image, FOV (enlargement ratio), and reconstruction function. The image generation parameters include parameters used in image processes such as volume rendering and MPR process executed in various medical diagnostic imaging apparatuses and image viewers. For example, in the case of an MPR process, reference coordinates, normal vector, slice thickness, range, and the like correspond to the parameters.

The range of the reconstruction parameters may be defined by attaching a positioning image showing a reconstruction range. In this case, a plurality of positioning images indicative of a plurality of reconstruction ranges are stored in one shared object.

[Supplementary Information 5: Key Image Information]

The key image information is information of the position and direction of a key image and image process attached at the stage of film reading or image diagnosis by a component on the PACS side. The shared object generating unit of each apparatus recognizes the corresponding image as the key image at a timing of displaying an image on an image viewer of the PACS and designating a specific image as a key image or a timing of performing an operation of attaching the image to a report or associating the image to a report (hyperlink). The image viewer retrieves and specifies a shared object of a series including the recognized image. As the identifier of the image, for example, information such as SOPInstanceUID conforming to the DICOM standard, z-axis coordinate position, the direction, the enlargement ratio, and WWW/WL at the time of observation is held as key image information. In the case of generating an MPR image, the position, direction, generation parameters of the MPR image as the key image may be used like the image generation parameters.

By holding the supplementary information, an image which can be compared with the image of last time at the start of film reading can be properly acquired.

(Operation)

The operation of the medical diagnostic imaging support system 1 will now be described.

Figure 6:
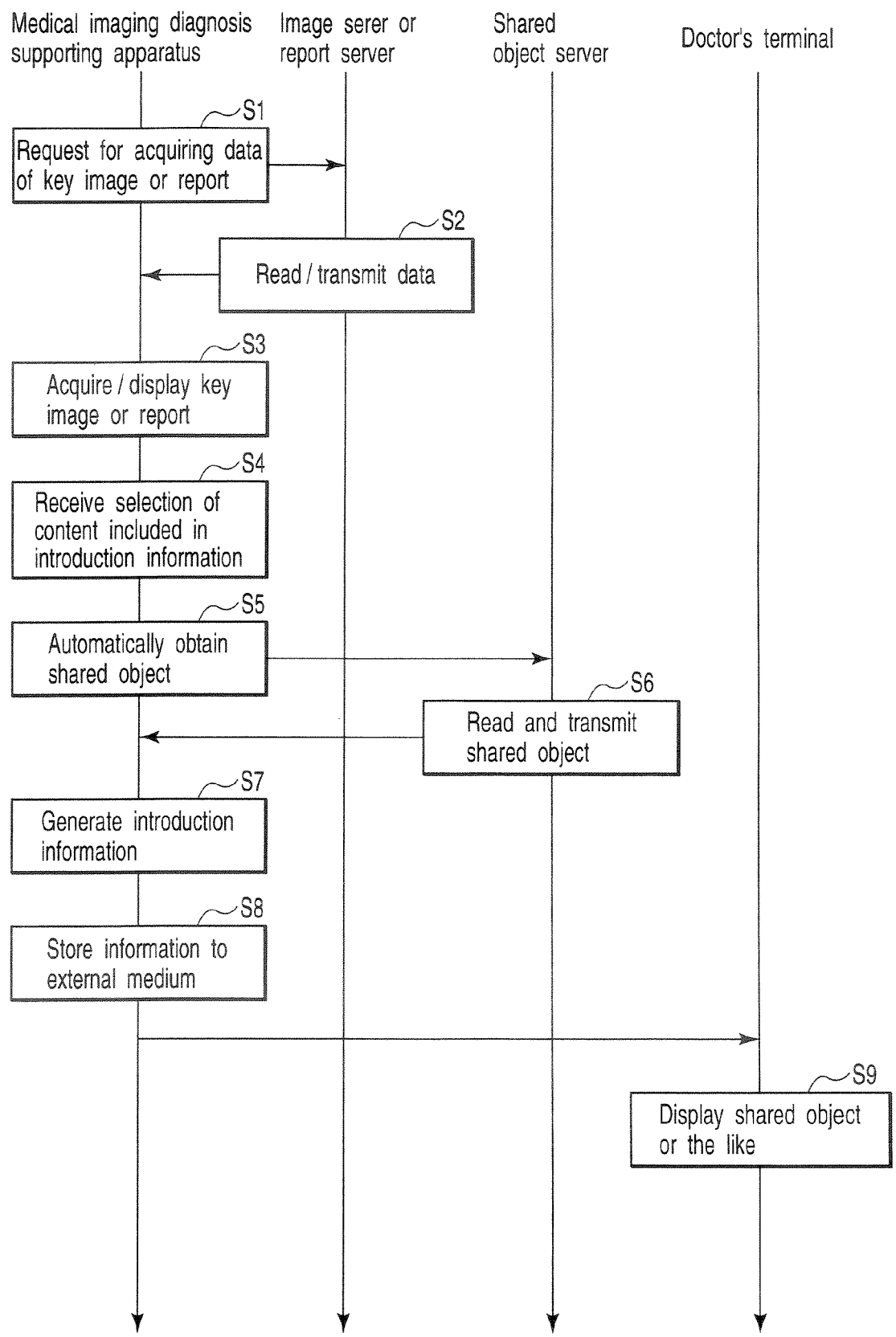
FIG. 6 is a sequence chart showing the flow of an introduction information generating process executed in the case where a patient is introduced from a current hospital (introducing side) to another hospital as an example of cooperation among hospitals.

FIG. 6 is a sequence chart showing the flow of introduction information generating process executed in the case where a patient is introduced from a hospital the patient goes (current hospital) to another hospital as an example of cooperation between hospitals. As shown in the diagrams, when a request for obtaining a key image or report of a patient to be introduced to another medical institute is entered by a doctor or the like, the medical imaging diagnosis supporting apparatus 10 transmits a request of acquiring the data to the image server 2 and the shared object server 4 in response to the request (step S1). The acquisition request is executed by using the patient information of the patient, the UID (Unique ID) or the like of the image data or report, or the like. In response to the request, the image server 2 or the report server 3 executes retrieving and reading operation and transmits the data to the medical imaging diagnosis supporting apparatus 10 via the network N (step S2).

The medical imaging diagnosis supporting apparatus 10 acquires image data or the like from the image server 2 or the like and displays the image data on the display unit 15 (step S3). The operator such as a doctor determines information as content to be included in introduction information while observing the displayed image data or the like and selects the information. The introduction information generating unit 13 receives the selected information to be included in the introduction information from the operator via the operation unit 17 (step S4). For example, in the case of selecting a report, only desired information in the report may be selected. As content included in the introduction information, predetermined number of key images and a report corresponding to the key images are selected.

Next, the introduction information generating unit 13 of the medical imaging diagnosis supporting apparatus 10 automatically transmits a request for acquiring a shared object having the same series ID as that of the selected key image or report to the shared object server 4 (step S5). In response to the request, the shared object server 4 executes retrieving and reading operation and transmits the requested shared object to the medial imaging diagnosis supporting apparatus 10 via the network N (step S6).

The introduction information generating unit 13 generates introduction information by using the shared object obtained from the shared object server 4 and the key image and the report selected in step S4 (step S7). The generated introduction information is stored in an external medium in the external medium drive 19 (step S8). Storage of the introduction information to an external medium is executed by using, for example, operation of a "storage" button from the operation unit 17 as a trigger. Moreover, the invention is not limited to the above. Alternatively, after the introduction information is generated, it may be automatically stored in an external medium at a predetermined timing.

Predetermined information in the shared object included in the introduction information may be reduced as necessary. The introduction information generated in step S7 may further include information which seems to be useful in diagnosis in the another hospital and is other than the key image, the report, and the shared object (hereinbelow, called "supplementary information"). Examples of the supplementary information are introducing-side hospital information, the patient information (the patient ID on the introducing-side hospital and, when it is known, the patient ID in the another hospital), a program for displaying the shared object, display style information (HTML/style sheet), exposure amount of the patient in a predetermined period, and the like. A converter or the like for displaying the shared object by using another software can be provided. In the case of including the supplementary information in the introduction information, the introduction information generating unit 13 obtains the supplementary information in the information pre-stored in the storing device 21 in accordance with the initial setting or manual setting in the introduction information generating process in step S7, and generates the introduction information including the supplementary information.

An external medium on which the introduction information is stored is provided by the patient himself/herself or by predetermined means such as mailing to the another medical institute. The key image, the shared object, and the like included in the introduction information stored in the external medium are used for, for example, setting of imaging parameters in an examination of this time, determination of a key image position, comparison with a result of an examination of this time, and the like in the another medical institute (step S9).

With the above-described configuration, the following effects can be obtained.

In the medical imaging diagnosis supporting apparatus, by selecting at least one of an image and a report provided for another hospital, a shared object having the same series ID as that of the image or report is automatically obtained, and introduction information including them is generated and stored in an external medium. Therefore, in an introducing-side institute, only by selecting an image or the like determined to be useful for a doctor or the like in another institute to which the patient is introduced, introduction information including a shared object corresponding to the image or the like can be easily and promptly generated. In the another institute, at the time of diagnosis based on medical information of the introducing-side institute, for example, image acquisition using the medical diagnostic imaging apparatus, imaging parameters and the like can be promptly and easily set so as to correspond to an examination in the past in the introducing-side institute. As a result, work loads on the introducing-side institute and another institute can be lessened, and a high-quality medical service can be realized by cooperation between the introducing-side institute and the another institute.

The introduction information may include, in addition to the key image, the report, and the shared object, as necessary, a program for displaying an exposure amount, the shared object, and the like. Therefore, various information can be transmitted from an introducing-side institute to another institute. Even in the case where the system of another institute does not handle a shared object, information provided from the introducing side can be used and images taken in the past can be recognized.

Second Embodiment

A second embodiment of the present invention will be described. A medical imaging diagnosis supporting apparatus according to the second embodiment stores, as introduction information, not image data and the like itself to an external medium but address information for accessing image data and the like to be provided to another institute via a network.

Figure 7:
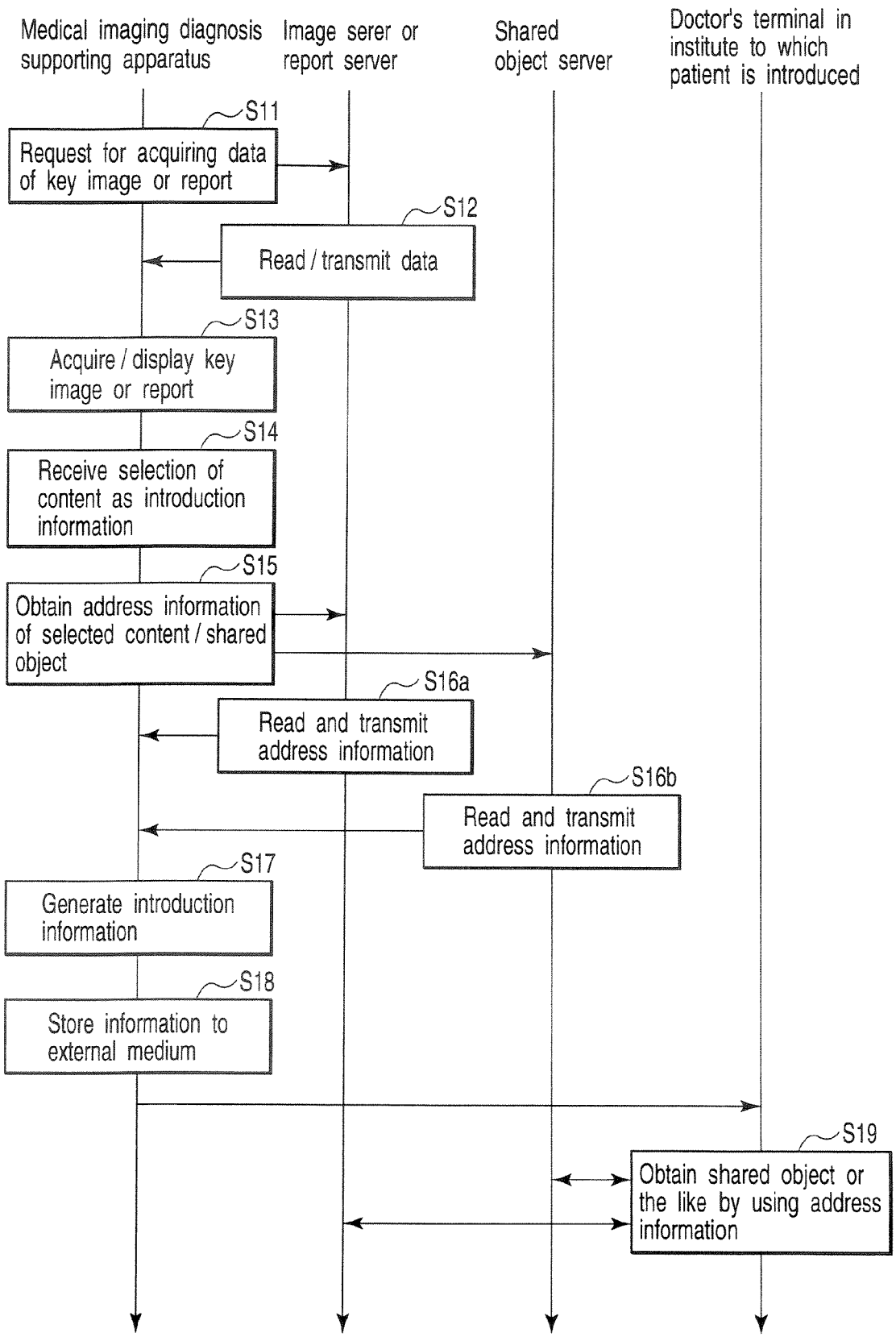
FIG. 7 is a sequence chart showing the flow of an introduction information generating process according to a second embodiment.

FIG. 7 is a sequence chart showing the flow of introduction information generating process according to the second embodiment. As shown in the diagram, in steps S11 to S14, processes similar to those of the steps S1 to S4 shown in FIG. 6 are executed.

Next, the introduction information generating unit 13 of the medical imaging diagnosis supporting apparatus 10 transmits a request for obtaining address information for accessing various kinds of content (that is, a selected key image, report information, and a shared object having the same series ID as that of the key image) to the various servers such as the image server 2, the report server 3, and the shared object server 4 via a network by using an ID for specifying the key image selected as content to be included in the introduction information and the series ID of the selected key image (step S15).

Next, each of the image server 2, the report server 3, and the shared object server 4 reads the address information of the various information with reference to an address information table in response to a request from the medical imaging diagnosis supporting apparatus 10, and transmits the address information to the medical imaging diagnosis supporting apparatus 10 via a network (step S16).

The medical imaging diagnosis supporting apparatus 10 obtains the address information of a key image, a shared object, and the like from each of the servers and generates introduction information by using the address information (step S17). The generated introduction information is stored in an external medium in the external medium drive 19 (step S18).

The introduction information generated in step S17 may include supplementary information. The supplementary information may include, other than the information examples mentioned in the first embodiment, for example, information necessary to access the various servers such as the image server 2 (a connection method (system such as ISDN or ADSL, telephone number, and password), and AE title and port information), and other information preferred to be included in the introduction information (such as the address of a hospital, the mail address of a manager, and the like). In the case where the supplementary information is included in the introduction information, the introduction information generating unit 13 automatically obtains corresponding information in information pre-stored in the storing device 21 and generates introduction information including the corresponding information by the introduction information generating process in step S17.

An external medium storing the introduction information is provided to another medical institute to which the patient is introduced by the patient himself/herself or predetermined means such as mailing. A doctor's terminal in the another medical institute obtains various information via the network by using the address information included in the introduction information stored in the external medium (step S19). The obtained key image, the shared object, and the like can be used for, for example, setting of imaging parameters of an examination of this time, determination of the position of a key image, and comparison with a result of the examination of this time in the another medical institute.

With the above configuration, the following effects can be obtained.

In the medical imaging diagnosis supporting apparatus, by selecting an image to be provided for another institute to which a patient is introduced, the address information of the selected image and the like and the address information of a shared object or the like having the same series ID as that of the image is automatically obtained, and introduction information including the address information is generated and stored in an external medium. Therefore, in an introducing-side institute, introduction information including information for accessing an image and a shared object useful for diagnosis in the another institute can be easily and promptly generated. In the another institute, by using the address information included in the introduction information, the image and the shared object useful for diagnosis can be accessed via a network. Therefore, for example, in the case where the capacity of an external medium is insufficient or in the case where diagnosis information such as an image itself is not stored in a external medium to prevent leakage of information and the like, effects similar to those of the first embodiment can be obtained.

Third Embodiment

For example, in the first embodiment, when an external medium does not have enough capacity to store all of content data such as key image data, a shared object, and the like, preferably, part of data is provided to another institute to which a patient is introduced via a network as necessary. In this case or also in the second embodiment, it is preferable to regulate kinds of data to be obtained by another institute from an introducing-side institute via a network from the viewpoint of security against information leakage and from the viewpoint of the network environment (mainly, line speed) of the another institute.

The medical diagnostic imaging support system of the third embodiment automatically determines content to be included in introduction information, whether or not various kinds of content are provided to another institute to which a patient is introduced, and a providing method in accordance with the security level, line speed, and the like of the another institute.

The configuration of the medical diagnostic image supporting system 1 of the third embodiment is similar to that shown in FIG. 3. Only elements having different functions will be described below.

The control unit 11 reads a dedicated program stored in the storing device 21 and develops the program on a not-shown memory, thereby realizing an introduction information determining function which will be described later.

The introduction information generating unit 13 executes a process according to the introduction information determining function (introduction information determining process) on the basis of data input from the operation unit 17 and various tables stored in the storing device 21. The process will be described in detail later.

The storing device 21 stores a dedicated program for executing the introduction information determining process and the various tables referred to in the introduction information determining process.

FIGS. 8 to 10 are diagrams showing various tables stored in the storing device 21 and referred to in the introduction information determining process.

Specifically, the table shown in FIG. 8 is a communication environment information table in which the line speed and the security level of each of institutes to which a patient is introduced are indicated in three levels; L (low level), M (intermediate level), and H (high level). By referring to the table, the introduction information generating unit 13 determines the line speed and the security level of an institute to which a patient is introduced.

The table shown in FIG. 9 is a table for a report, showing, in the case of sending a report from an introducing-side institute to another institute to which a patient is introduced via a network, whether transmission via a network can be performed or not on the basis of the relation between the line speed and the security level. By referring to the table, the introduction information generating unit 13 determines whether a report desired to be included in introduction information can be transmitted via a network or not on the basis of the relation between the line speed and the security level.

The table shown in FIG. 10 is a table for an image, showing, in the case of sending a key image from an introducing-side institute to another institute to which a patient is introduced via a network, whether transmission via a network can be performed or not on the basis of the relation between the line speed and the security level. By referring to the table, the introduction information generating unit 13 determines whether a key image desired to be included in introduction information can be transmitted via a network or not on the basis of the relation between the line speed and the security level.

(Introduction Information Determining Function)

Next, the introduction information determining function of the medical diagnostic imaging support system 1 will be described. The function is provided to automatically determine content to be included in introduction information in accordance with the security level, line speed, and the like of an institute to which a patient is introduced. The content varies depending on priority of an introducing-side institute (or the institute to which a patient is introduced) on provision of introduction information by an external medium or provision by network communication. The description will be given below about the introduction information determining function corresponding to various modes such as priority on external media, priority on network communication, and the like.

Figure 11:
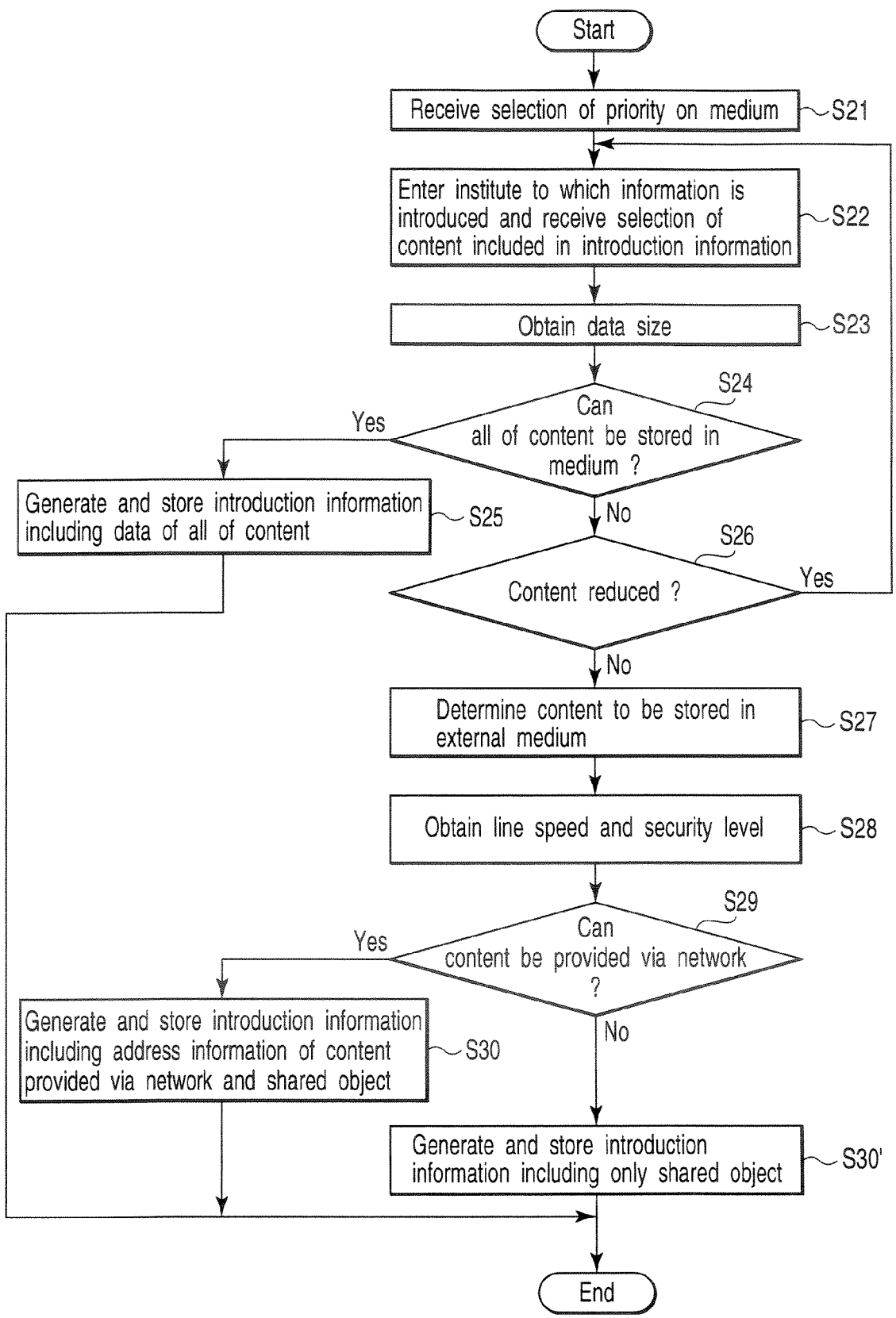
FIG. 11 is a flowchart showing the flow of introduction information determining process in the case where priority is placed on an external medium.

FIG. 11 is a flowchart showing the flow of the introduction information determining process in the case where priority is placed on an external medium. As shown in the diagram, first, selection of priority on a medium, entry of an introducing-side institute, and selection of content to be included in introduction information are executed (steps S21 and S22). Specifically, a key image and a report to be included in introduction information are selected, for example, in order shown in the steps S1 to S4 in FIG. 6. The key image and the like included in the introduction information are selected, for example, in accordance with the processes in step S11 to S14 in FIG. 7. To make the following description concrete, it is assumed that a plurality of key images and reports corresponding to the key images are selected in step S12. Although priority is generally placed on a medium by using the operation unit 17, the invention is not limited to the method. For example, priority on a medium may be automatically placed by initial setting.

Next, the introduction information generating unit 13 obtains the data size of each of the key image, the report, and the shared object having the same series ID as that of the key image selected in step S22 (step S23), and determines whether the content can be stored in an external medium or not (step S24). When it is determined that all of the content can be stored in an external medium, the introduction information generating unit 13 acquires data of the corresponding content from, for example, the image server 2, the shared object server 4, and the like, generates introduction information including the data, and stores the introduction information into an external medium (step S25).

On the other hand, when it is determined that all of the content cannot be stored in an external medium, the introduction information generating unit 13 urges the operator to reduce the content selected in step S22 (that is, reduce the data size of the content) (step S26). In the case of reducing the content by, for example, decreasing 10 key images selected in step S22 to five images in response to the urging, the processes in steps S22 to S26 are repeatedly executed.

In the case where the operator does not reduce the content, the introduction information generating unit 13 determines whether the content is stored in an external medium or not on the basis of the pre-set priority and the data size of the content (step S27). It is assumed that only the shared object is stored in an external medium.

The introduction information generating unit 13 obtains the line speed and the security level of another institute to which a patient is introduced (step S28). The line speed and the security level of the another institute are obtained by referring to the table stored in the storing device 21 on the basis of the information of the another institution entered in step S22. The introduction information generating unit 13 determines whether content which is not stored in the external medium can be provided via a network or not on the basis of the obtained line speed and the security level of the another institute (step S29).

When it is determined that at least one of the image data and the report can be provided via the network, the introduction information generating unit 13 obtains the address information for accessing content determined to be able to be provided via the network and the shared object having the same series ID as that of the content selected in step S22, generates introduction information by using the address information and the shared object, and stores the introduction information to an external medium (step S30). When it is determined that the image data and the report cannot be provided via the network, the introduction information generating unit 13 obtains only the shared object, generates introduction information by using the shared object, stores the introduction information to an external medium, and finishes the introduction information generating process (step S30').

In step S29 or S30, for example, as described in the first embodiment, preferably, a shared object to which the same series ID as that of the content selected in step S22 is given is automatically obtained as it is or in a form in which predetermined items are reduced.

In the introduction information determining process placing priority on a medium, for example, when an institute to which a patient is introduced is an institute A and all of selected content cannot be stored in an external medium, the line speed and the security level of the institute A are obtained. On the basis of the line speed and the security level, whether the content can be provided via a network or not is determined. As shown in FIG. 8, since both of the line speed and the security level of the institute A are "M", it is determined that the selected report can be provided via a network and, on the other hand, the selected key image cannot be provided via a network. Therefore, introduction information including the shared object itself and the address information of the report is stored in an external medium.

Next, the introduction information determining process in the case where priority is placed on a network will be described.

FIG. 12 is a flowchart showing the flow of the introduction information determining process in the case where priority is placed on a network. As shown in the diagram, first, selection of priority on a network, entry of an institute to which a patient is introduced, and selection of content to be included in introduction information are executed (steps S31 and S32). To make description concrete, it is assumed that a key image and a report are selected as content to be included in introduction information.

Next, the introduction information generating unit 13 obtains the line speed and security level of the institute to which a patient is introduced with reference to the tables stored in the storing device 21 on the basis of the information of the institute to which a patient is introduced, entered in step S32 (step S33). On the basis of the obtained line speed and the security level, the introduction information generating unit 13 determines whether the key image, the report, and the shared object having the same series ID as that of the key image and the report selected in step S32 can be transmitted via a network or not. When it is determined that they can be transmitted, the introduction information generating unit 13 generates introduction information including the addresses of all of content and stores the introduction information on an external medium (steps S34 and S35).

When it is determined that the content cannot be transmitted, the introduction information generating unit 13 obtains the data size of each of all of the content (step S36) and determines whether the content can be stored in an external medium or not (step S37) When it is determined that all of the content can be stored in an external medium, the introduction information generating unit 13 acquires data of the corresponding content from, for example, the image server 2, the shared object server 4, and the like, generates introduction information including the acquired data, and stores the introduction information in an external medium (step S38). On the other hand, when it is determined that all of the content cannot be stored in an external medium, the introduction information generating unit 13 urges the operator to reduce the content selected in step S32 (step S39) In the case where the operator reduces the content, the processes in steps S36 to S38 are repeatedly executed.

On the other hand, in the case where the operator does not reduce the content, the introduction information generating unit 13 determines which one of the selected image and the selected report is stored in an external medium on the basis of the pre-set priority, the data size of the content, the capacity of the external medium, and the like (step S40). In the case where it is determined to store the selected image or report on an external medium, the introduction information generating unit 13 generates introduction information including the selected image or report and the shared object, or introduction information including the selected image or report, the shared object, and supplementary information, and stores the generated introduction information on an external medium (step S41). On the other hand, when it is determined that both of the selected image and report are not stored in an external medium, the introduction information generating unit 13 generates introduction information including only the shared object, or including the shared object and supplementary information, stores the generated information on an external medium, and finishes the introduction information generating process (step S42).

In the introduction information determining process placing priority on a network, for example, when an institute to which a patient is introduced is an institute A, as shown in FIG. 8, the line speed and the security level of the institute A are "M". It is determined that the selected report can be provided via a network and, on the other hand, the selected key image cannot be provided via a network. Therefore, introduction information including the shared object and the address information of the report or, according to the capacity of the external medium, introduction information further including the key image is stored in an external medium.

With the above-described configuration, the following effects can be obtained.

The medical imaging diagnosis supporting apparatus automatically determines content to be included in introduction information, whether various kinds of content are introduced to another institute or not, and a content providing method in accordance with the security level and line speed of the another institute, the capacity of an external medium, and the like. Therefore, while assuring safety against information leakage, for example, even in the case of including a large amount of images or the like in introduction information, an optimum providing method can be determined. As a result, work loads on an introducing-side institute and an another institute to which a patient is introduced at the time of transferring the patient can be lessened, and high-quality medical service by cooperation between the introducing-side institute and the another institute can be realized.

The medical imaging diagnosis supporting apparatus can optionally select a medium priority mode or a network priority mode and optimally determine content of introduction information and a method of providing the information in the selected mode. Therefore, an introducing-side institute or an another institute to which a patient is introduced can realize provision of introduction information in a desired form, and high-quality medical service can be realized by cooperation between the introducing-side institute and the another institute.

Fourth Embodiment

In the first to third embodiments, introduction information including entity data such as image data or introduction information including address information for obtaining image data or the like via a network later on is generated and stored in an external medium. A medical imaging diagnosis supporting apparatus according to a fourth embodiment transmits introduction information generated by any of the methods described in the foregoing embodiments to an apparatus of an institute to which a patient is introduced directly via a network without storing the information on an external medium.

Specifically, for example, when introduction information including entity data of an image or the like is generated in step S7 in FIG. 6, the transmitting/receiving unit 23 transmits the introduction information to a doctor's terminal in an institute to which a patient is to be introduced via a network under the control of the control unit 11. For example, when introduction information including address information of a shared object or the like is generated in step S17 in FIG. 7, the transmitting/receiving unit 23 transmits the introduction information to a doctor's terminal in an institute to which a patient is to be introduced via a network under the control of the control unit 11. Further, when introduction information is generated in any of steps S35, S38, S41, and S42 in FIG. 12, the transmitting/receiving unit 23 transmits the introduction information to a doctor's terminal in an institute to which a patient is introduced via a network under the control of the control unit 11. Such transmission of introduction information is executed by, for example, operation on the "transmission" button of the operation unit 17 as a trigger. However, the trigger is not limited to operation on the "transmission" button. When introduction information is generated, it may be automatically transmitted to a doctor's terminal in an institute to which a patient is introduced at a predetermined timing.

With the above configuration, introduction information generated by an introducing-side institute can be provided promptly and easily via a network to an apparatus in an institute to which a patient is introduced. As a result, work loads on the introducing-side institute and the institute to which a patient is introduced can be lessened, and high-quality medical service by cooperation between the introducing-side institute and the institute to which a patient is introduced can be realized.

The present invention is not limited to the foregoing embodiments but can be embodied by modifying the components without departing from the spirit of the invention. The invention may be modified as follows.

(1) The functions in the embodiments can be also realized by installing a program for executing the functions on a computer such as a workstation and developing the program on a memory. A program capable of making the computer execute the method may be distributed by being stored in a recording medium such as a magnetic disk (floppy (registered trademark) disk, hard disk, or the like), an optical disk (CD-ROM, DVD, or the like), or a semiconductor memory.

(2) In the first embodiment, introduction information including a selected key image, a selected report, and a shared object corresponding to the image and report is generated. The invention is not limited to the configuration. For example, introduction information including only a shared object corresponding to a selected key image or the like may be generated. In this case, it is sufficient to generate introduction information including only the shared object in step S7 in accordance with the flow of processes in FIG. 6. Also in the second embodiment, it is sufficient to generate introduction information including only the address information of a shared object corresponding to a selected key image or the like. In this case, it is sufficient to obtain only address information of a shared object in step S15 and generate introduction information including the address information in step S17 in accordance with the flow of processes in FIG. 7.

(3) In the third embodiment, from the viewpoints of line speed and security against information leakage in an institute to which a patient is introduced, content to be included in introduction information and the method of providing the content are determined. However, the invention is not limited to this method of determination. The determination may be also made from the viewpoint of only the line speed or the security against information leakage in an institute to which a patient is introduced. In this case as well, it is sufficient to make determination using, as a reference, the line speed or the security against information leakage in an institute to which a patient is introduced in step S28 (or S34) in accordance with the flow of processes in FIG. 11 (or FIG. 12).

(4) In each of the foregoing embodiments, to designate a key image or the like desired to be included in introduction information, the information is once displayed on the display unit 15. However, the invention is not limited to this case. For example, a predetermined key image or the like included in the introduction information may be selected by initial setting or a manual operation without being displayed.

By properly combining a plurality of components disclosed in the foregoing embodiments, the invention can be variously modified. For example, some of all of the components in the embodiments may be deleted. Further, the components in different embodiments may be properly combined.

What is claimed is:

1. A medical imaging diagnosis supporting apparatus including a central processing unit, comprising:
    a selecting unit which specifies an ID information by selecting at least one of an image and a report of a patient, each of which includes ID information;
    an retrieving unit which provides a medical object to a second medical facility by retrieving the medical object having the specified ID information from a storing device which stores a plurality of medical objects including one or more positioning images from a previous medical examination at a first medical facility, imaging parameter information from the previous medical examination at the first medical facility, and ID information; and
    a generating unit which receives the medical object from the retrieving unit and generates, using the central processing unit, at least one of
    a resultant image by considering at least one of the positioning images included in the retrieved medical object, and at least one of the imaging parameter information included in the retrieved medical object, and
    a resultant report by considering at least one of the positioning images included in the retrieved medical object, at least one of the imaging parameter information included in the retrieved medical object, and obtained medical information from the patient at the first medical facility.

2. The medical imaging diagnosis supporting apparatus according to claim 1, wherein the retrieving unit provides the medical object to the second medical facility by retrieving the medical object in a portable medium.

3. The medical imaging diagnosis supporting apparatus according to claim 1, wherein the retrieving unit provides the medical object to the second medical facility by retrieving the medical object via a network.

4. The medical imaging diagnosis supporting apparatus according to claim 1, wherein the generating unit further generates at least one of a resultant positioning image and resultant imaging parameter information associated with at least one of the resultant image and the resultant report.

5. The medical imaging diagnosis supporting apparatus according to claim 4, wherein the generating unit generates at least one of the resultant image and the resultant report and transmits at least one of the resultant image and the resultant report to another apparatus via a network.

6. The medical imaging diagnosis supporting apparatus according to claim 4, further comprising:
    a determining unit which determines whether the selected image should be included in the medical object generated at the first medical facility or not on the basis of communication environment information preliminarily obtained; and
    a transmitting unit which transmits the generated at least one of a resultant image and a resultant report to another apparatus via a network,
    wherein in the case where the determining unit determines that the selected image should be included in the medical object, the generating unit generates at least one of the resultant image and the resultant report including the selected image or information for another apparatus to obtain the selected image via a network.

7. The medical imaging diagnosis supporting apparatus according to claim 6, wherein the communication environment information includes at least one of network speed and safety against information leakage.

8. The medical imaging diagnosis supporting apparatus according to claim 4, further comprising:
    a determining unit which determines whether the selected report should be included in the medical object generated at the first medical facility or not on the basis of pre-set communication environment information; and
    a transmitting unit which transmits the generated at least one of a resultant image and a resultant report to another apparatus via a network,
    wherein in the case where the determining unit determines that the selected report should be included in the medical object, the generating unit generates at least one of the resultant image and the resultant report including the selected report or information for another apparatus to obtain the selected report via a network.

9. The medical imaging diagnosis supporting apparatus according to claim 8, wherein the communication environment information includes at least one of network speed and safety against information leakage.

10. The medical imaging diagnosis supporting apparatus according to claim 4, further comprising:
    a determining unit which, in the case where the image is selected by the selecting unit, determines whether the selected image is able to be stored in a portable medium or not on the basis of the capacity of the portable medium and data size of the selected image; and
    a storing unit which stores the generated at least one of resultant image and resultant report in the portable medium,
    wherein in the case where the determining unit determines that the selected image can be stored in the portable medium, the generating unit generates at least one of the resultant image or the resultant report including the selected image and, in the case where the determining unit determines that the selected image cannot be stored in the portable medium, the generating unit generates at least one of the resultant image and the resultant report including information for the another apparatus to obtain the selected image via a network.

11. The medical imaging diagnosis supporting apparatus according to claim 4, further comprising:
    a determining unit which, in the case where the report is selected by the selecting unit, determines whether the selected report is able to be stored in a portable medium or not on the basis of the capacity of the portable medium and data size of the selected report; and
    a storing unit which stores the generated at least one of resultant image and resultant report in the portable medium,
    wherein in the case where the determining unit determines that the selected report can be stored in the portable medium, the generating unit generates at least one of the resultant image and the resultant report including the selected report in the portable medium and, in the case where the determining unit determines that the selected report cannot be stored in the portable medium, the generating unit generates at least one of the resultant image and the resultant report including information for another apparatus to obtain the selected report via a network.

12. The medical imaging diagnosis supporting apparatus according to claim 1, wherein the generating unit further generates ID information associated with at least one of the resultant image and the resultant report.

13. The medical imaging diagnosis supporting apparatus according to claim 1, wherein the ID information is series ID information.

14. A medical imaging diagnosis supporting method implemented by a medical imaging diagnosis supporting apparatus including a central processing unit, the method comprising:
   specifying an ID information by selecting at least one of an image and a report of a patient each of which includes ID information;
   providing a medical object to a second medical facility by retrieving the medical object including the specified ID information from a storing device which stores a plurality of medical objects including one or more positioning images from a previous medical examination at a first medical facility, imaging parameter information from the previous medical examination at the first medical facility, and ID information;
   receiving the medical object from the providing; and
   generating, using the central processing unit of the medical imaging diagnosis supporting apparatus, at least one of
   a resultant image by considering at least one of the positioning images included in the retrieved medical object, and at least one of the imaging parameter information included in the retrieved medical object, and
   a resultant report by considering at least one of the positioning images included in the retrieved medical object, at least one of the imaging parameter information included in the retrieved medical object, and the obtained medical information from the patient at the first medical facility.

15. The medical imaging diagnosis supporting method according to claim 14, further comprising providing the medical object to the second medical facility by retrieving the medical object in a portable medium.

16. The medical imaging diagnosis supporting method according to claim 14, further comprising providing the medical object to the second medical facility by retrieving the medical object via a network.

17. The medical imaging diagnosis supporting method according to claim 14, wherein, the generating further comprises generating at least one of a resultant positioning image and resultant imaging parameter information associated with at least one of the resultant image and the resultant report.

18. The medical imaging diagnosis supporting method according to claim 17, wherein, in generating further generates at least one of the resultant image and the resultant report and transmits at least one of the resultant image and the resultant report to another apparatus via a network.

19. The medical imaging diagnosis supporting method according to claim 17, further comprising:
   determining whether the selected image should be included in the medical object generated at the first medical facility or not on the basis of communication environment information preliminarily obtained;
   in the case where it is determined that the selected image should be included in the medical object, generating at least one of the resultant image and the resultant report including the selected image or information for another apparatus to obtain the selected image via a network.

20. The medical imaging diagnosis supporting method according to claim 19, wherein the communication environment information includes at least one of network speed and safety against information leakage.

21. The medical imaging diagnosis supporting method according to claim 17, further comprising:
   determining whether the selected report should be included in the medical object generated at the first medical facility or not on the basis of pre-set communication environment information;
   in the case where it is determined in the determining step that the selected report should be included in the medical object, generating at least one of the resultant image and the resultant report including the selected report or information for another apparatus to obtain the selected report via a network.

22. The medical imaging diagnosis supporting method according to claim 21, wherein the communication environment information includes at least one of network speed and safety against information leakage.

23. The medical imaging diagnosis supporting method according to claim 17, further comprising:
   in the case where the image is selected in the selecting step, determining whether the selected image is able to be stored in a portable medium or not on the basis of the capacity of the portable medium and data size of the selected image; and
   in the case where it is determined in the determining step that the selected image can be stored in the portable medium, the generating further generates at least one of the resultant image or the resultant report including the selected image;
   in the case where it is determined in the determining step that the selected image cannot be stored in the portable medium, the generating further generates at least one of the resultant image or the resultant report including information for the another apparatus to obtain the selected image via a network.

24. The medical imaging diagnosis supporting method according to claim 17, further comprising:
   in the case where the report is selected in the selecting step, determining whether the selected report is able to be stored in a portable medium or not on the basis of the capacity of the portable medium and data size of the selected report;
   in the case where it is determined in the determining step that the selected report can be stored in the portable medium, the generating further generates at least one of the resultant image or the resultant report including the selected report;
   in the case where it is determined in the determining step that the selected report cannot be stored in the portable medium, the generating further generates at least one of the resultant image or the resultant report including information for another apparatus to obtain the selected report via a network.

25. The medical imaging diagnosis supporting method according to claim 14, wherein the generating further generates ID information associated with at least one of the resultant image and the resultant report.

26. The medical imaging diagnosis supporting method according to claim 14, wherein the ID information is series ID information.

* * * * *